(12) United States Patent
Shekalim

(10) Patent No.: US 9,980,836 B2
(45) Date of Patent: May 29, 2018

(54) ANTI-RESTENOSIS CORONARY STENT

(71) Applicant: Avraham Shekalim, Nesher (IL)

(72) Inventor: Avraham Shekalim, Nesher (IL)

( * ) Notice: Subject to any disclaimer, the term of this patent is extended or adjusted under 35 U.S.C. 154(b) by 120 days.

(21) Appl. No.: 14/654,846

(22) PCT Filed: Dec. 25, 2013

(86) PCT No.: PCT/IL2013/051068
§ 371 (c)(1),
(2) Date: Jun. 23, 2015

(87) PCT Pub. No.: WO2014/102787
PCT Pub. Date: Jul. 3, 2014

(65) Prior Publication Data
US 2015/0342766 A1 Dec. 3, 2015

Related U.S. Application Data

(60) Provisional application No. 61/745,773, filed on Dec. 25, 2012.

(51) Int. Cl.
| | | |
|---|---|---|
| A61F 2/958 | (2013.01) | |
| A61F 2/92 | (2013.01) | |
| A61F 2/94 | (2013.01) | |
| A61F 2/07 | (2013.01) | |

(52) U.S. Cl.
CPC .......... *A61F 2/94* (2013.01); *A61F 2/07* (2013.01); *A61F 2/92* (2013.01); *A61F 2/958* (2013.01)

(58) Field of Classification Search
CPC ...... A61F 2/04; A61F 2/06; A61F 2/07; A61F 2/82; A61F 2/844; A61F 2/92; A61F 2/94; A61F 2/95; A61F 2/958; A61F 2002/072; A61F 2002/823; A61F 2002/825
See application file for complete search history.

(56) References Cited

U.S. PATENT DOCUMENTS

| | | | | |
|---|---|---|---|---|
| 4,800,882 A | * | 1/1989 | Gianturco | A61F 2/885 606/194 |
| 4,907,336 A | * | 3/1990 | Gianturco | A61F 2/885 140/71 R |
| 4,969,458 A | * | 11/1990 | Wiktor | A61F 2/885 623/1.11 |
| 5,041,126 A | * | 8/1991 | Gianturco | A61F 2/885 604/104 |
| 5,314,444 A | * | 5/1994 | Gianturco | A61F 2/885 604/104 |
| 5,342,387 A | * | 8/1994 | Summers | A61F 2/88 606/198 |
| 5,354,309 A | * | 10/1994 | Schnepp-Pesch | A61F 2/82 606/198 |

(Continued)

*Primary Examiner* — Ryan J Severson
(74) *Attorney, Agent, or Firm* — Mark M. Friedman

(57) ABSTRACT

A stent designed to reduce risk of restenosis opens peripherally within a blood vessel so that, when deployed, a periphery of the stent has a longitudinal opening spanning a length of the stent, the longitudinal opening spanning between 30 and 170 degrees. The stent does not scrape or penetrate the blood vessel wall when it opens because the peripheral surface of the stent slides along an interior blood vessel wall without leading edges of the peripheral surface contacting the interior blood vessel wall.

10 Claims, 17 Drawing Sheets

(56) References Cited

U.S. PATENT DOCUMENTS

| | | | |
|---|---|---|---|
| 5,540,713 A * | 7/1996 | Schnepp-Pesch | A61F 2/82 606/198 |
| 5,607,445 A * | 3/1997 | Summers | A61F 2/88 606/198 |
| 5,632,771 A * | 5/1997 | Boatman | A61F 2/885 606/198 |
| 5,766,192 A * | 6/1998 | Zacca | A61B 17/320725 606/159 |
| 5,954,765 A * | 9/1999 | Ruiz | A61F 2/92 606/194 |
| 6,080,191 A * | 6/2000 | Summers | A61F 2/88 623/1.16 |
| 6,273,908 B1 * | 8/2001 | Ndondo-Lay | A61F 2/885 606/194 |
| 6,932,091 B2 * | 8/2005 | Frazier | A61F 2/86 128/898 |
| 7,647,931 B2 * | 1/2010 | Pflueger | A61F 2/203 128/848 |
| 7,815,674 B1 * | 10/2010 | Ragazzo | A61F 2/844 623/1.23 |
| 7,846,202 B2 * | 12/2010 | Bates | A61F 2/0077 623/1.15 |
| 7,867,275 B2 * | 1/2011 | Bates | A61F 2/82 623/1.42 |
| 8,187,315 B1 * | 5/2012 | Clauson | A61B 17/02 623/1.1 |
| 2002/0173838 A1 * | 11/2002 | Frazier | A61F 2/86 623/1.15 |
| 2003/0171801 A1 * | 9/2003 | Bates | A61F 2/07 623/1.13 |
| 2005/0163821 A1 * | 7/2005 | Sung | A61F 2/88 424/426 |
| 2007/0276465 A1 * | 11/2007 | Mongrain | A61F 2/885 623/1.15 |
| 2009/0105806 A1 * | 4/2009 | Benjamin | A61F 2/92 623/1.15 |
| 2013/0073023 A1 * | 3/2013 | Mongrain | A61F 2/885 623/1.2 |
| 2015/0272750 A1 * | 10/2015 | Roth | A61F 2/92 623/1.15 |
| 2015/0342766 A1 * | 12/2015 | Shekalim | A61F 2/92 623/1.11 |

* cited by examiner

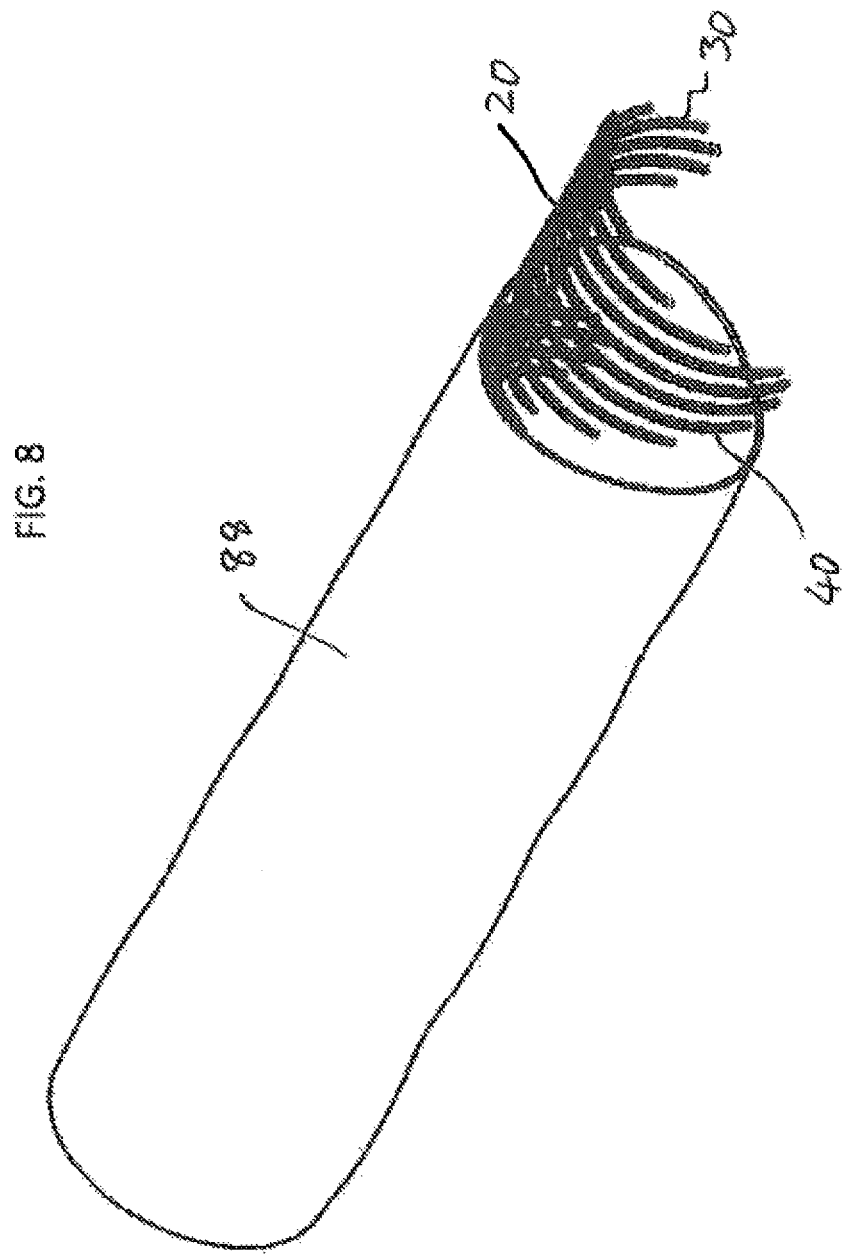

ANTI-RESTENOSIS CORONARY STENT

FIELD AND BACKGROUND OF THE INVENTION

The present invention relates to apparatuses and methods for stents, and, more particularly to stents that opens in a blood vessel in a manner that avoids damage to arterial walls and dramatically reduces restenosis.

Angioplasty is commonly used to treat blockages of the coronary arteries, or peripheral arteries such as limbs. The balloon inserted into the narrow artery smashes the plaque against the artery wall. In the angioplasty procedure there is no choice but to expand the balloon until it causes damage to the internal stratum of the artery. This is done in order to reduce artery elasticity, preventing its contraction to the original state after balloon extraction.

A stent is a tube-like structure used in conjunction with angioplasty to permanently hold open an artery. Although stent implantation does not necessarily cause damage to artery wall stratum, and artery elasticity can be maintained to prevent artery contraction, the stent itself narrows the artery wall substantially in comparison to a balloon alone. In addition, during implantation of the stent the artery wall stratum is damaged and ripped, not because of artery wall extension but because of shifting and scraping of artery wall by the wires (i.e. struts) of the stent. The stent wires (struts) that generate the stent, work as blades that peel and penetrate the artery wall.

The occurrences of these scraping/lacerations are necessarily in the direction of a length and periphery of the artery. When the stent opens, the stent's periphery is widened. While the stent widens its periphery, the length of the stent contracts. Significant efforts are being made to develop a stent having a geometric structure such that the length of the stout will not be affected while the stent expands in the artery. However, even a stent that did not contract would still cause scraping and penetration of wires against the walls of the artery due to peripheral expansion. It should be noted that the stent's expansion in the artery, is on account of artery length. In order to solve this problem, an attempt exists to develop a stent that whose degree of contraction correlates with the degree of contraction of the artery.

Unfortunately, analyses that have addressed this issue demonstrate that as a whole this correlation is not possible. Accumulation of "rough" plaque in artery wall damages the artery's capability to expand its periphery and contracts its length with unity in a predictable matter. Therefore, up to now it has not been possible to correlate between stent contractions to artery contractions.

The relation between artery wall damage and restenosis has been researched extensively. Two or three weeks after stent implantation, there can be a return of artery blockage. This creates thrombosis that can be treated mainly by anti coagulating drugs. The chronic phase occurs generally between three to six months post implantation. The mechanism that causes the blockage in the chronic phase is not known. What is known is that there is a connection between artery wall injury that occurs while stent implantation and tissue growth within that creates a neointima layer after several months. It is also known that the artery can react to the stent, perceive it as a foreign object that penetrates artery wall, and respond with an immune system response that causes tissue growth. This leads to further narrowing of the artery near the stent or inside the stent.

In recent years, in order to find a solution to the problem of restenosis after angioplasty, there has been an effort to implant a stent coated with a given medication that is released over time. One of these stents is "full degradable" and the medication is released while the stent degrades. Medications of these sorts are supposed to treat the problem of tissue growth between and upon the stent wall, which develops several weeks after implantation. These drug-eluting stents are being tested clinically.

This problem of thrombosis, which appears in the artery a short while after implantation, is treated to some extent by the use of increased dosage of anti coagulating medications. Anti coagulating drugs and slow-release drugs prevent tissue growth within the stent. Stents coated with such medications treat the symptoms of a tear in the artery stratum after it happens but do not prevent the injury itself.

Significantly, moreover, the stents coated with drugs are very expensive. Although these stents inhibit tissue growth and thus may reduce the risk of restenosis from scar tissue and cell proliferation, to use these stents requires satisfying certain conditions and doing so requires a unique and complex procedure. One condition that must be satisfied, for example, is creating a drug that will be released in full in the two weeks time post implantation until several months later. In addition, the drug coating the stent should be a thin layer to avoid shortening the artery's diameter post implantation. The drug should also be flexible and not disengage during stent extension. These conditions make the product very expensive.

There is a compelling need for an apparatus that reduces the problems of prior art stents, namely, reducing scraping and penetration of artery walls by the stent when the stent opens, and damage to the artery wall when the stent length contracts during peripheral expansion.

SUMMARY OF THE PRESENT INVENTION

One aspect of certain embodiments of the present invention is directed to a stent capable of opening peripherally within a blood vessel from a closed position to an open position such that in the open position a periphery of the stent has a longitudinal opening (swath) spanning a length of the stent, the longitudinal opening spanning between approximately 30 and 160 degrees about the longitudinal axis of the stent.

A further aspect of certain embodiments of the present invention is a stent capable of opening peripherally within a blood vessel from a closed position to an open position such that in the open position a periphery of the stent has a longitudinal opening spanning a length of the stent, the longitudinal opening spanning between approximately 30 and 160 degrees, and more preferably between about 90 and about 120 degrees.

According to a further aspect of certain embodiments of the present invention, the open state of the stent is defined by a stent-opening balloon which has a predefined fully inflated state corresponding to the desired degree of opening of the stent to provide the longitudinal opening of the desired angular extent.

A still further aspect of certain embodiments of the present invention is directed to a stent made of a material, the stent comprising a periphery including a peripheral surface, the periphery not having a cut-out opening surrounded by the material, the stent capable of opening peripherally within a blood vessel from a closed position to an open position such that the peripheral surface slides along an interior blood vessel wall in a direction of expansion of the blood vessel wall, i.e., without any edge of the material advancing across a tissue surface.

Thus, according to the teachings of an embodiment of the present invention, there is provided a stent for maintaining an open state of a vessel wall, the stent comprising: (a) an elongated backbone defining a direction of elongation; and (b) a plurality of ribs interconnected with the backbone and projecting therefrom in a direction perpendicular to the direction of elongation, the plurality of ribs assuming an initial state in which the ribs have curved forms so that the elongated backbone and the plurality of ribs lie substantially on a virtual cylinder of a first diameter, the ribs being configured for plastic deformation to an open state in which the ribs lie substantially on a virtual cylinder of a second diameter greater than the first diameter, wherein the ribs are parallel sided or tapering away from the backbone, and wherein each of the ribs follows a curve lying in a plane perpendicular to the direction of elongation.

According to a further feature of an embodiment of the present invention, the ribs are mechanically interconnected solely via the backbone.

According to a further feature of an embodiment of the present invention, each of the ribs is untethered other than its attachment to the backbone.

According to a further feature of an embodiment of the present invention, the plurality of ribs project from both sides of the backbone in staggered relation, and wherein, in the initial state, ends of at least a subset of the ribs are interdigitated.

According to a further feature of an embodiment of the present invention, in the open state, the ribs do not span an entirety of the virtual cylinder of the second diameter, leaving a continuous swath along the virtual cylinder free from the stent.

According to a further feature of an embodiment of the present invention, lengths of the ribs vary in an undulating pattern along a length of the backbone.

According to a further feature of an embodiment of the present invention, tips of the ribs are configured to remain inwardly curled relative to the virtual cylinder of a second diameter.

According to a further feature of an embodiment of the present invention, there is also provided a flexible sleeve deployed around the backbone and the plurality of ribs, the flexible sleeve being formed from biodegradable material.

There is also provided according to the teachings of an embodiment of the present invention, a stent kit comprising the aforementioned stent and a stent-opening balloon to be inflated within the stent to open the stent from the initial state to the open state, the balloon having a predefined fully inflated state defining the open state of the stent, wherein, in the open state, the ribs do not span an entirety of the virtual cylinder of the second diameter, leaving a continuous swath along the virtual cylinder free from the stent.

There is also provided according to the teachings of an embodiment of the present invention, a stent kit comprising: (a) a stent comprising an expandable structure including a plurality of ribs, the expandable structure assuming an initial state in which the ribs lie substantially on a virtual cylinder of a first diameter, the expandable structure being configured for plastic deformation to an open state in which the ribs lie substantially on a virtual cylinder of a second diameter greater than the first diameter; and (b) a stent-opening balloon to be inflated within the stent to open the stent from the initial state to the open state, the balloon having a predefined fully inflated state defining the open state of the stent, wherein the stent is configured such that, in the open state, the ribs do not span an entirety of the virtual cylinder of the second diameter, leaving a continuous swath along the virtual cylinder free from the stent.

According to a further feature of an embodiment of the present invention, the continuous swath spans an angle of between 30 degrees and 170 degrees about a central axis of the stent.

According to a further feature of an embodiment of the present invention, the continuous swath spans an angle of between 90 degrees and 160 degrees about a central axis of the stent.

According to a further feature of an embodiment of the present invention, the ribs form at least part of a lattice structure.

Another aspect of the present invention relates to a method for deploying a stent within a blood vessel according to the various features and properties described herein.

These and other features, aspects and advantages of the present invention will become better understood with reference to the following drawings, descriptions and claims.

BRIEF DESCRIPTION OF THE DRAWINGS

Various embodiments are herein described, by way of example only, with reference to the accompanying drawings, wherein:

FIG. 8 illustrates a stent according to an aspect of the present invention surrounded by a sleeve of biodegradable flexible material;

DETAILED DESCRIPTION OF THE INVENTION

Figure 1:
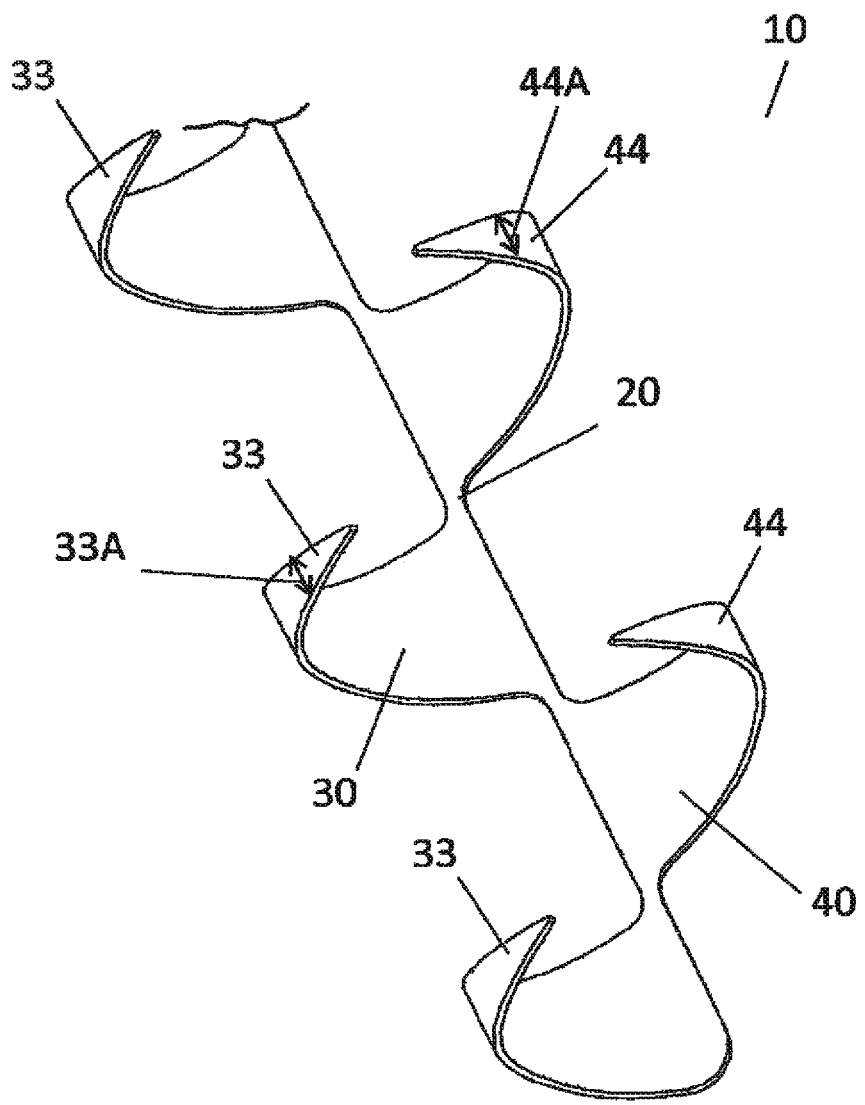
FIG. 1 is a perspective view of a stent in open position in accordance with one embodiment of the present invention.

The following detailed description is of the best currently contemplated modes of carrying out the invention. The description is not to be taken in a limiting sense, but is made merely for the purpose of illustrating the general principles of the invention, since the scope of the invention is best defined by the appended claims. In particular, although reference may be made to coronary stents and to angioplasty, such references are merely by way of non-limiting exemplary applications, but should not be considered to limit the present invention to such applications.

The present invention generally provides a stent for an artery that reduces risks of restenosis. The stent is capable of opening peripherally within an artery from a closed position to an open position such that in the open position a periphery of the stent has a longitudinal opening spanning a length of the stent, the longitudinal opening spanning between approximately 30 and 160 degrees. This allows blood to flow through the artery including in the area of the stent without blockage by the stent, thus dramatically reducing restenosis. Furthermore, the stent preferably does not scrape or penetrate the blood vessel wall when it opens peripherally. Instead, the peripheral surface of the stent slides along an interior blood vessel wall in a direction of expansion of the blood vessel wall without leading edges of the peripheral surface contacting the interior blood vessel wall. The peripheral surface, which may have a backbone and arcuate ribs, is sufficiently inwardly curved so that when the stent opens peripherally in the blood vessel, linear surfaces of the peripheral surface contact the interior blood vessel wall in a sliding motion.

In contrast to prior art stents, in which the struts of the stent may scrape against the arterial wall during expansion of the stent, the stent of the present invention may successfully avoid damage to the arterial wall caused by scraping and penetration. This may be due in part to the fact that the peripheral surface of the stent moves without leading edges of a cut out portion in a direction of expansion of the blood vessel wall and because the peripheral surface curves inwardly. As a result, linear surface of the arcuate branches of the stent may slide along the arterial wall when opening and may avoid scraping or penetrating the arterial wall. In further contrast to prior art stents, which contract lengthwise when they expand peripherally, i.e. when they open, the stent of the present invention may successfully open peripherally without contracting lengthwise. This may be due in part to the stable spinal column (backbone) of the stent of the present invention that is rigid longitudinally and flexible in other directions (i.e. crosswise) and which may have an overall shape as a continuous straight line in the longitudinal direction of the stent. In still further contrast to prior art stents, which after opening are flush against a significant portion of the surface area of the internal wall of the artery that the stent is inside of, causing an immune system response at the points of contact, the stent of the present invention, after opening, may have fewer points of contact with the arterial wall since it has a lot of space where the stent is not flush against the interior arterial wall. When the stent is open, ends 33 of left arcuate branches 30 do not extend far enough to reach ends 44 of right arcuate branches 40 and the respective ends 33, 44 do not touch one another either axially or radially. Consequently, a large part of the artery's periphery may not be in contact with or flush against the stent (i.e. 30 to 160 degrees at any length) and this may prevent the body's immune response of rejection of a foreign object from developing in those uncovered areas. In contrast to prior art art stents, which do not permit an uninterrupted flow path of blood along a full length of the stent in the artery, the stent of the present invention in an open position leaves between approximately 30 and 160 degrees open at all lengths of the stent thus allowing an uninterrupted flow path of blood along the artery 60. Most preferably, the open angle is between about 90 and about 120 degrees relative to the central axis of the stent. The continuous flow of blood along the artery wall 66 throughout the length of the stent may greatly reduce the opportunity for scar tissue to form adjacent the stent (and not only in the uncovered areas) and greatly reduce risk of re-blocking the vessel. In still further contrast to prior art stents, the stent of the present invention may be ideally suited for resisting restenosis by successfully addressing the three critical problems causing restenosis for which previous stents did not provide an answer.

The principles and operation of a method and system for an anti-restenosis coronary stent according to the present invention may be better understood with reference to the drawings and the accompanying description.

Figure 5:
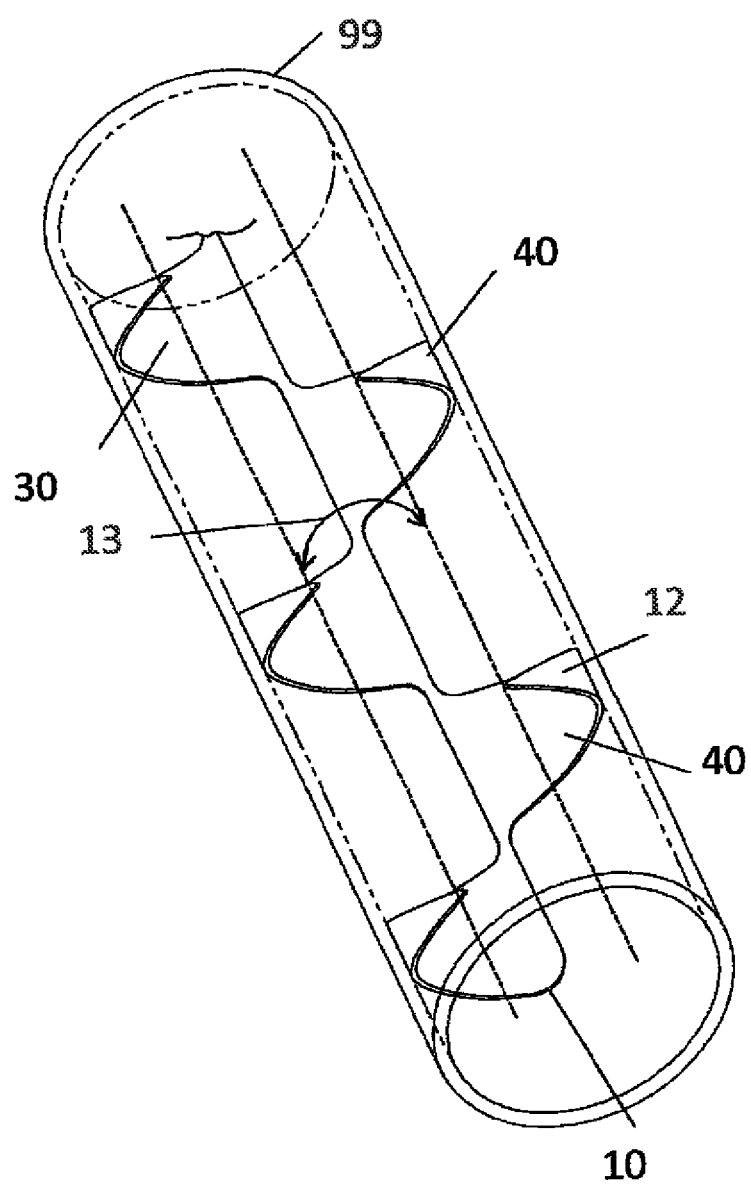
FIG. 5 is a perspective view of the stent of the present invention as in FIG. 1 inside a cylinder in open position and showing a longitudinal opening throughout a length of the stent.

FIG. 5 shows stent 10 inside a cylindrical tube 99 which may be a blood vessel. As seen in FIG. 5, a stent 10 may have a periphery 12 that may have a longitudinal opening 13 spanning a length of stent 10. As seen from the curved arrow depicting an angular range around the periphery of the cylindrical form in FIG. 5, longitudinal opening 13 may span between approximately 30 and 160 degrees around the central axis of the stent and may have no material of stent 10. Accordingly, a longitudinal surface (adjacent longitudinal opening 13 of stent 10) of a blood vessel 60 spanning a length of the stent may be free of any material of stent 10.

As seen from FIG. 1, stent 10 may comprise a spine (backbone) 20 in the shape of a straight continuous line such that spine 20 is collinear with a length and longitudinal direction of stent 10. Spine 20 may be flexible enough to be inserted through blood vessels which wind their way through the body and may be bendable in all directions except in the longitudinal direction since spine 20 may be shaped as a continuous straight line and may be sufficiently rigid in this direction. Accordingly, stent 10 may avoid contracting during its peripheral expansion (i.e. opening).

Figure 6:
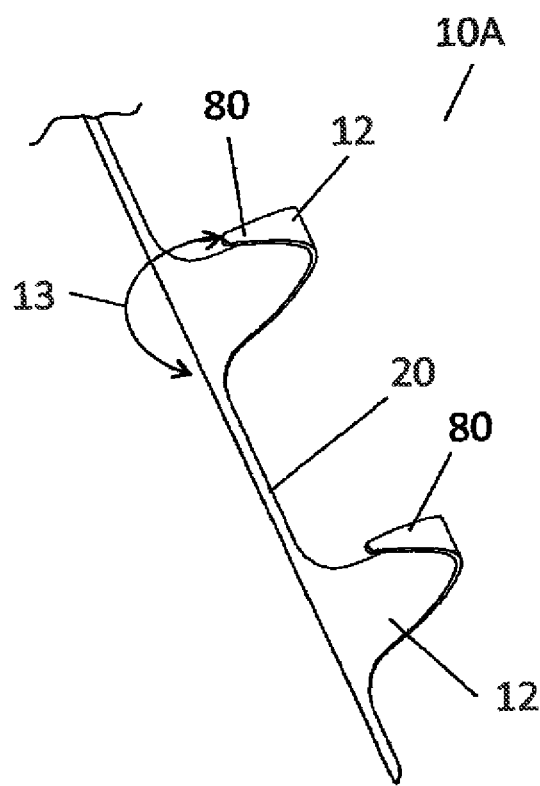
FIG. 6 is a perspective view of a further embodiment of the stent of the present invention in open position.

Stent 10 may also include a plurality arcuate branches or ribs projecting from spine 20, at a minimum from one side of stent 10 (see FIG. 6). Stent may have both a plurality of left arcuate branches 30 projecting from a left side of spine 20 spaced apart from one another and a plurality of right arcuate branches 40 projecting from a right side of spine 20 spaced apart from one another. In FIG. 6, stent 10A may have a periphery 12 comprised of arcuate branches 80 extending from only one side of spine 20. Although branches 80 in FIG. 6 appear to leave a longitudinal opening 13 of more than 160 degrees, this drawing is not intended to be precise in this regard and actually branches 80, in an open position, would preferably extend further around the periphery of the cylinder and may cross a point 180 degrees from spine 20, i.e. opposite spine 20.

Figure 7:
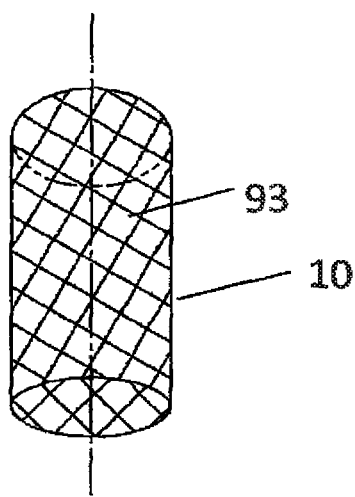
FIG. 7 shows a perspective view of an alternative embodiment of a stent of the present invention in an artificially flattened position.
Figure 9A:
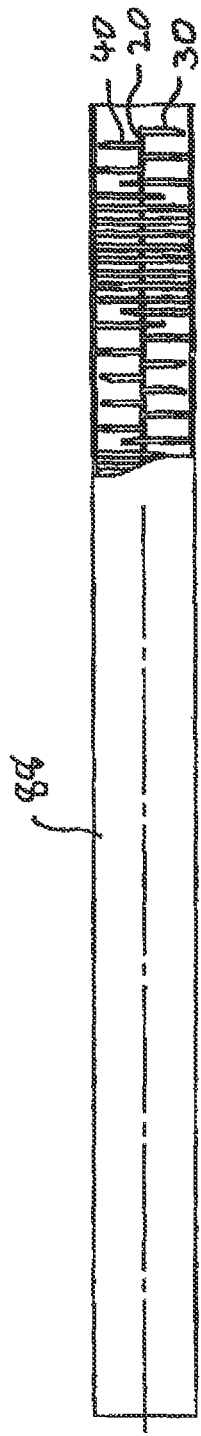
FIGS. 9A and 9B illustrate the stent of FIG. 8 in a closed and an open state, respectively.
Figure 9B:
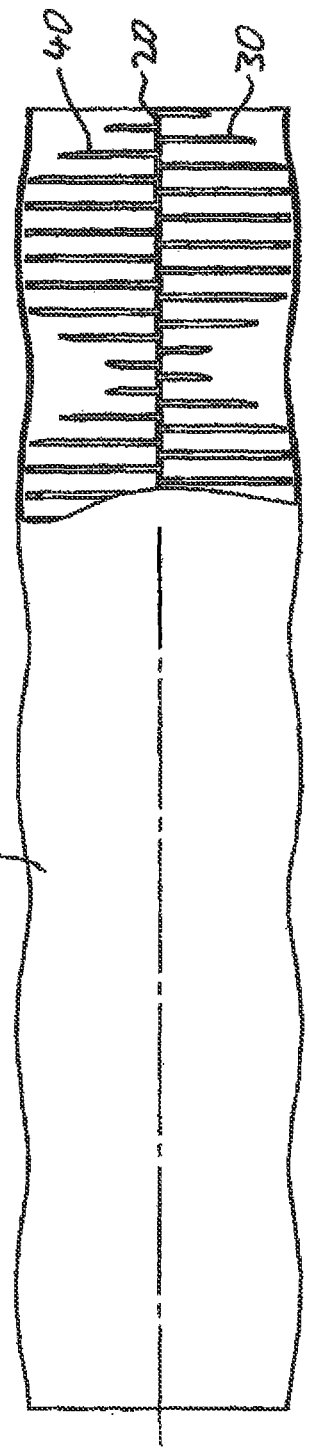
Figure 10B:
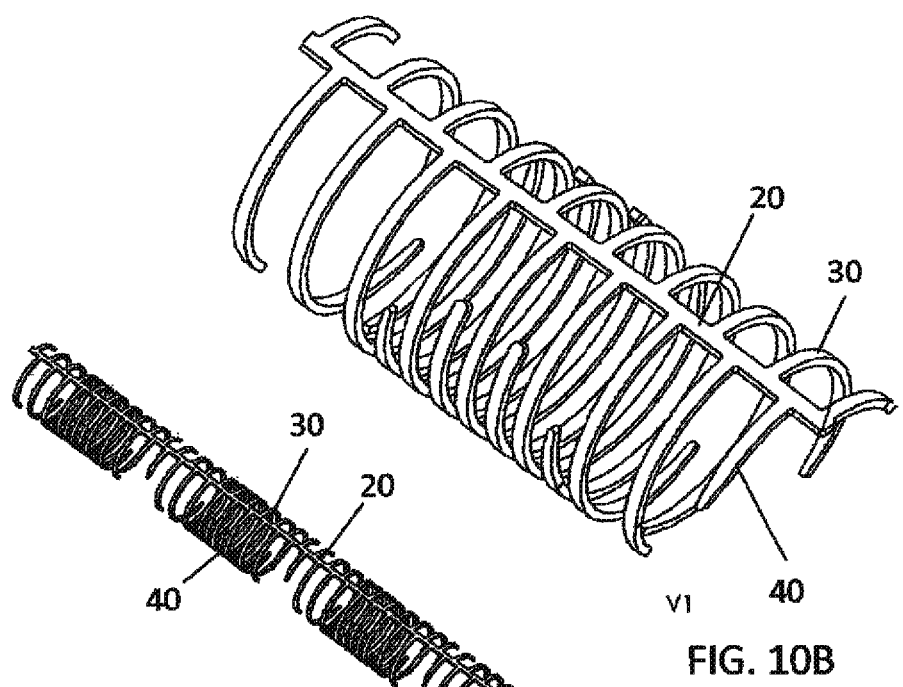
FIGS. 10A and 10B are isometric views of a support structure from the stent of FIG. 8, shown in its initial (closed) state.
Figure 10A:
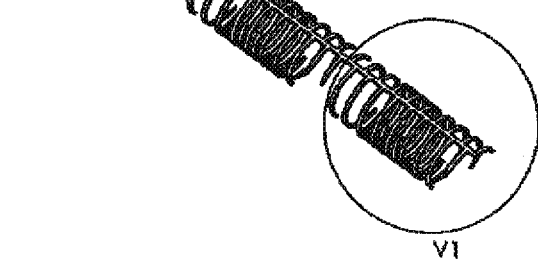

Stent 10 need not necessarily have arcuate branches as shown in FIGS. 1-5. For example, in one embodiment stent 10 may have a body comprised of a lattice structure. FIG. 7 illustrates a stent 10 with a lattice structure 93 in an artificially flattened position for the purpose of illustrating its structure. Although this embodiment does not avoid advancing of edges of the stent material across tissue, it still benefits from all the advantages of leaving a swath of vessel tissue along the vessel free from the stent's mechanical support structure. In this embodiment, periphery 12 of stent 10 may have a longitudinal opening spanning a length of stent 10 and spanning between 30 and 160 degrees so that a blood vessel adjacent stent 10 would be free of material adjacent it along a longitudinal surface along the side of the blood vessel. In particular, after stent 10 opens, between 30 to 160 degrees of a blood vessel wall 66 of the blood vessel 60 is not covered by stent 10 when stent 10 is in an open position.

Figure 11:
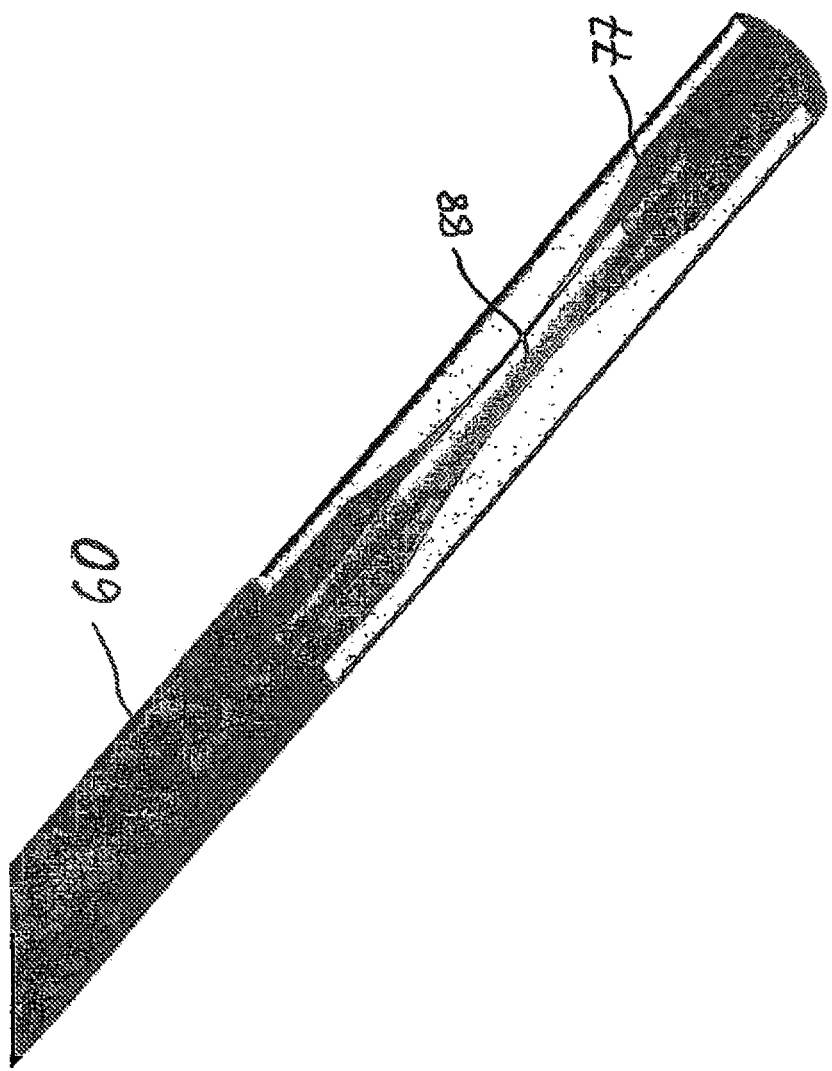
FIG. 11 is a schematic, partially cut-away isometric view of a stent kit including the stent of FIG. 8 in its initial state, deployed within a blood vessel.
Figure 12:
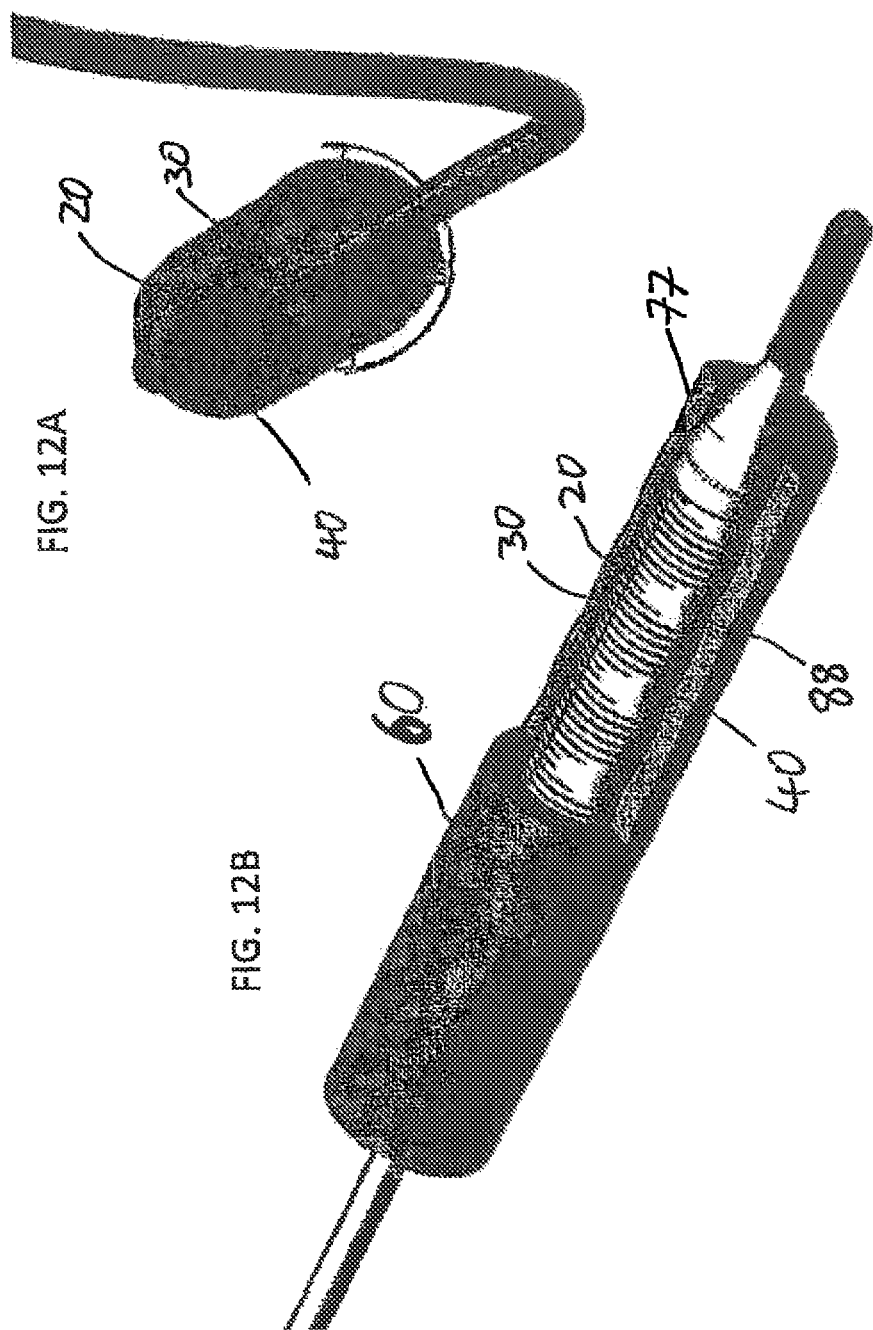
FIGS. 12A and 12B are further schematic views similar to FIG. 11 after inflation of a deployment balloon.
Figure 13:
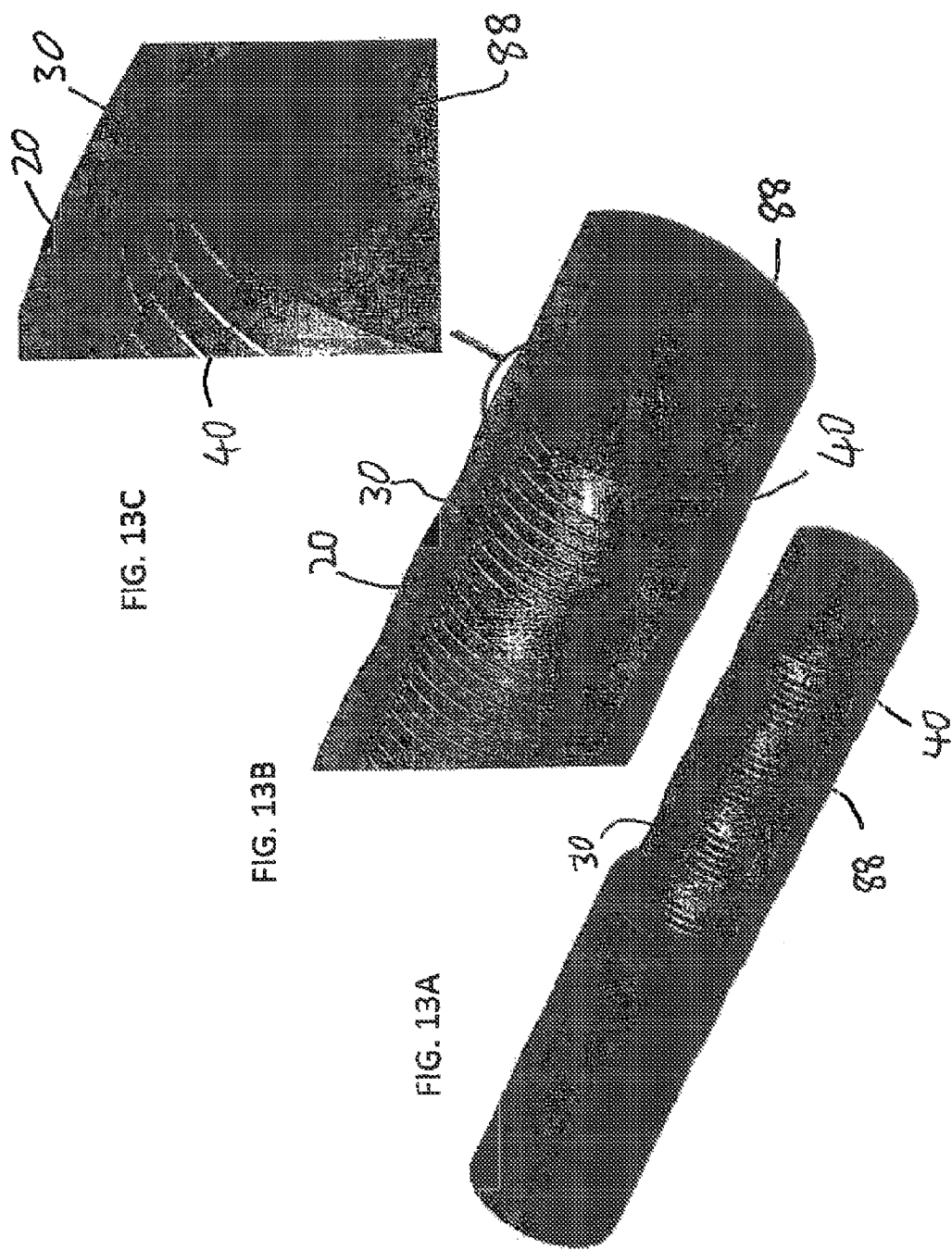
FIGS. 13A-13C are schematic views similar to FIG. 12B after removal of the deployment balloon.

Parenthetically, in all cases in which the stents of the present invention are referred to as reaching a certain degree of opening, this corresponds to the degree of opening that is reached by fully inflating the associated balloon 77 of a balloon catheter for deploying the stent (see FIGS. 11, 12A and 12B). Furthermore, when angles are stated for the part of the periphery of the blood vessel spanned by the stent, or for the width of the open swath where no structural material of the stent is present, these angles are measured relative to a central axis of the balloon at the end of the deployment process (see FIG. 12B), which may not necessarily correspond to the axis of the vessel, which may to some extent conform around the stent structure after removal of the balloon.

As can be seen from FIG. 1, the curvature of left and right arcuate branches 30, 40 may be in three dimensions. As seen from FIG. 1, left arcuate branch 30 and right arcuate branch 40 may be configured so that neither branch 30, 40 reaches the other branch 30, 40 either axially or radially, such that they remain "untethered" other than at their connection to the backbone (spine) 20. In the embodiment of arcuate branches 30, 40 shown in FIG. 1, left and right arcuate branches 30, 40 are configured in an alternating manner along a length of the spine so that at a given length of spine 20 one arcuate branch, i.e. either left arcuate branch 30 or right arcuate branch 40, projects therefrom. As a result, at any length of the spine 20 a periphery 12 of stent 10, which may be generally circular in cross-section, may be so open that the open area along the periphery may span between approximately 30 and 160 degrees. Accordingly, a large part of the periphery of stent 10 may be completely open at any length of stent 10. Furthermore, since the open area of periphery 12 of stent 10 extends throughout the length of stent 10, when stent 10 is open in a blood vessel such as an artery 60, arterial blood can flow without interruption throughout a length of stent 10 The uninterrupted flow blood may thwart formation of scar tissue along interior artery wall 66 that would trigger an immune system response by the body to a foreign body.

A width of arcuate branches 30, 40 may vary throughout a length of stent 10. For example, more support and hence a greater width may be needed at and near the ends of stent 10. Accordingly, the flexibility of stent 10 may vary at different points along its length.

Figure 2B:
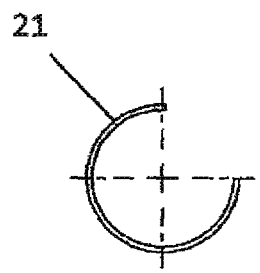
FIG. 2B is a top view of the stent of FIG. 2A in open position.
Figure 2A:
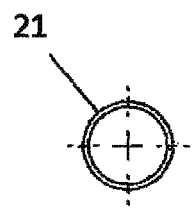
FIG. 2A is a top view of the stent of FIG. 1 in closed position.
Figure 2C:
FIG. 2C is a top view of a stent in accordance with one embodiment of the present invention in closed position.
Figure 2D:
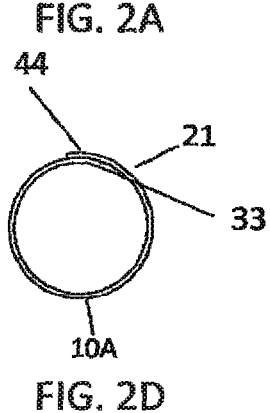
FIG. 2D is a top view of the stent of FIG. 2C in open position.

FIG. 2A shows a top view of stent 10 in closed position whereas FIG. 2B shows a similar view of stent 10 after stent 10 has opened within the blood vessel, e.g., an artery. In an alternative embodiment where stent 10 is more closed, FIGS. 2C and 2D show closed and open positions respectively of a stent 10A in accordance with an alternative embodiment of the present invention. Although periphery 12 of stent 10 may be generally circular, periphery 12 may also deviate from a circle. For example, there may be slightly flattened portions along ends 33, 44 of arcuate branches 30, 40.

Periphery 12 of stent 10 may include a peripheral surface. As can be seen from FIG. 1, periphery 12 does not having a cut-out opening surrounded by a material of stent 10 which could scrape or poke the blood vessel when stent 10 opens. It should be appreciated that when stent 10 opens peripherally, blood vessel 60 simultaneously expands. Accordingly, stent 10 opens peripherally within a blood vessel 60 from a closed position to an open position such that the peripheral surface 12A slides along an interior blood vessel wall 66 in a direction of expansion of the blood vessel wall. Branches 30, 40 are substantially normal to spine 20 and any edges of branches 30, 40 would not form leading edges that could grate against artery wall 66 in a direction different from the natural expansion of the blood vessel wall 66 as blood vessel 60 expands. Rather, a peripheral surface of the branches 30, 40 may slide along an interior artery wall 66 in a direction of expansion of the arterial wall 66.

Figure 3:
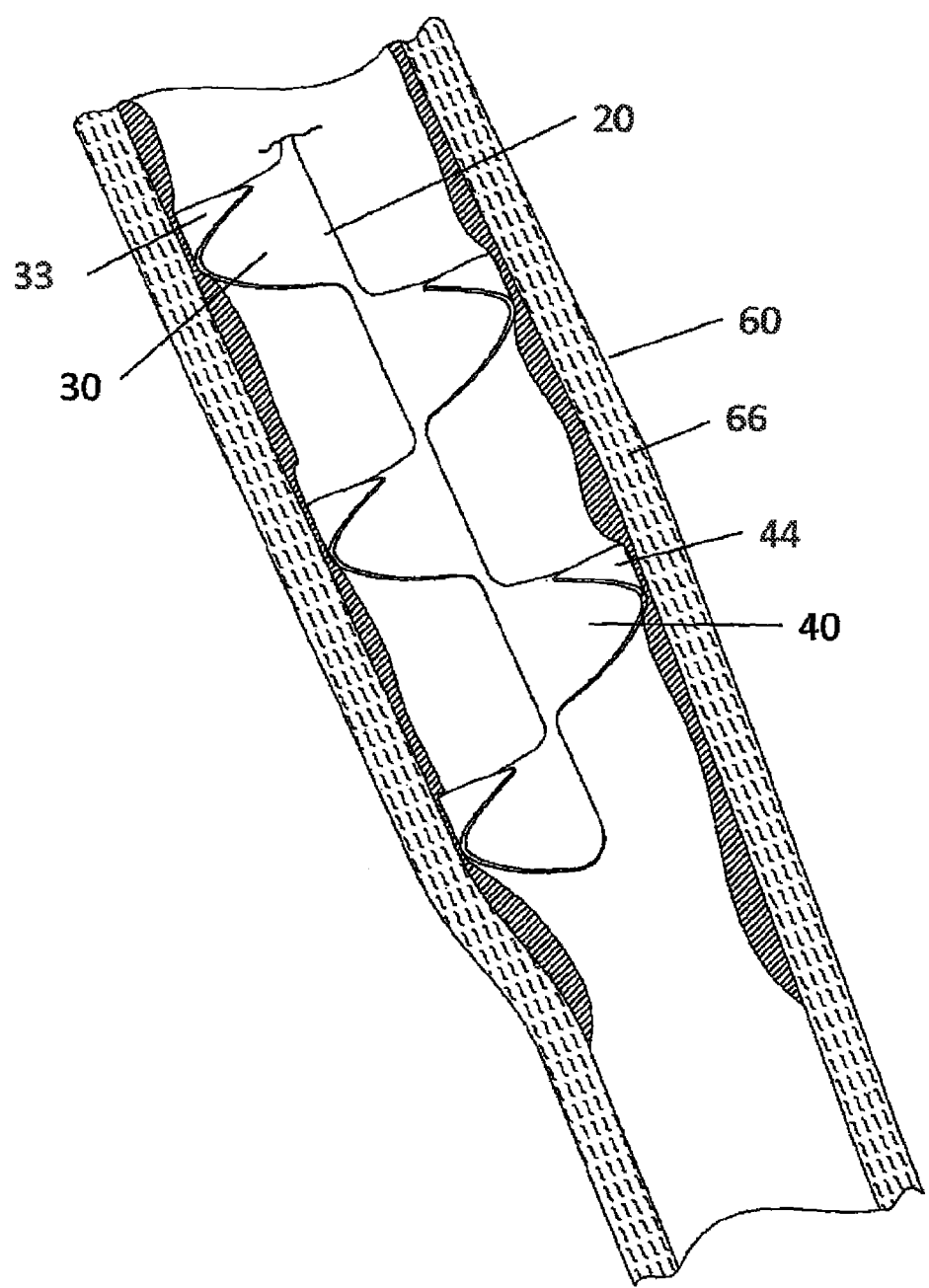
FIG. 3 is a perspective view of the stent of FIG. 1 in open position inside a blood vessel in accordance with an embodiment of the present invention.
Figure 4:
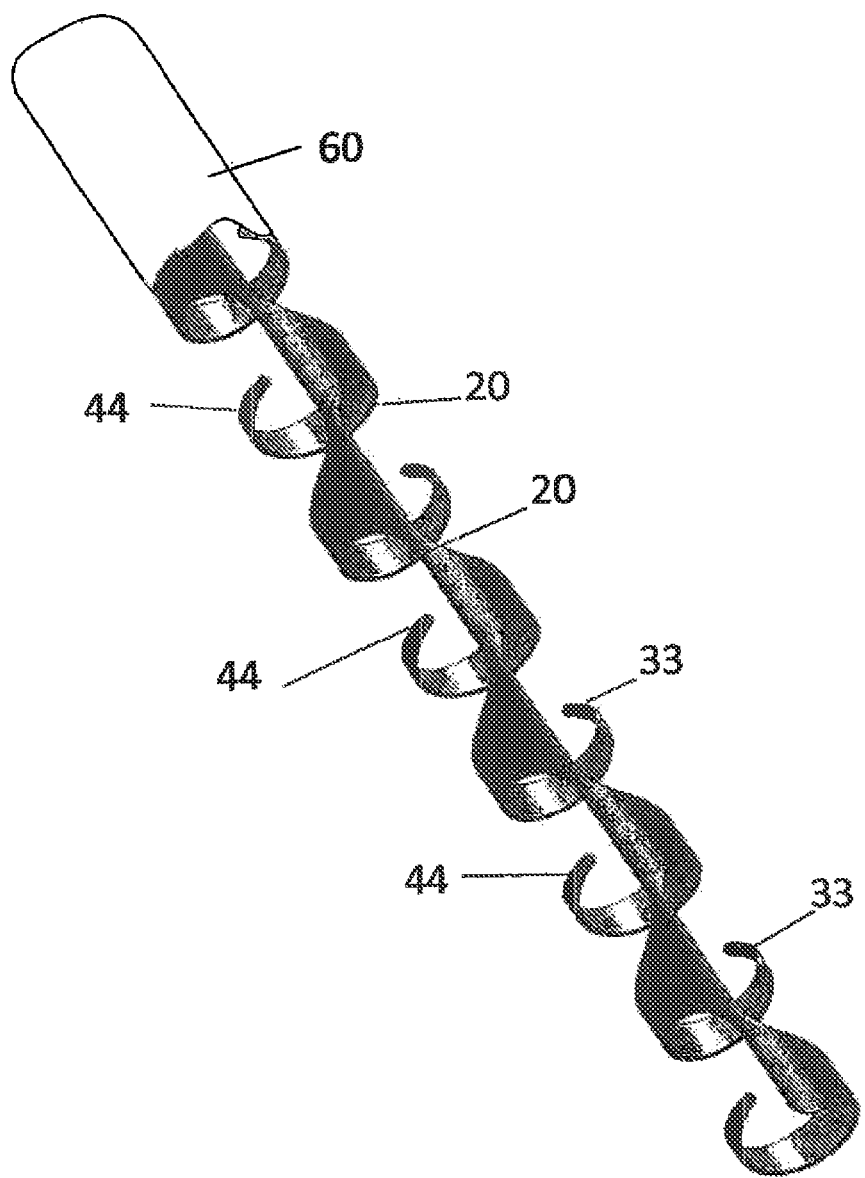
FIG. 4 is a perspective view of a stent in accordance with the present invention in closed position.

In addition, as seen from FIG. 3, the arcuate branches 30, 40 may be sufficiently inwardly curved so that when the stent 10 opens peripherally while inside an artery 60 having an interior arterial wall 66, the edges 33, 44 of the arcuate branches 30, 40 may not poke or penetrate arterial wall 66. Instead, linear surfaces 33A, 44A of the arcuate branches 30, 40 may contact interior artery wall 66 by sliding against interior arterial wall 66 when stent 10 opens peripherally.

The term artery 60 and interior arterial wall 66 should be understood to refer broadly to a blood vessel 60 and an interior blood vessel wall 66.

According to certain preferred implementations of the present invention, a biodegradable sleeve covers the metallic stent in order to give peripheral support, preferably combined with drug eluting, to the circumference of the blood vessel.

During expansion of the vessel, there is a risk that particulate material may be released into the blood stream from the layers of the vessel wall and/or from material resulting from the disease process. In order to reduce the risk of such release of particles into the blood stream, certain preferred implementations of the present invention provide a flexible sleeve 88 (FIGS. 8-9B and 13A-13C) which is temporarily deployed around the stent structure during deployment. The sleeve is preferably formed from biodegradable material which is effective during deployment to retain particulate material out of the main blood stream, but breaks down over a period of days or weeks to leave the open-sided structure described above. Most preferably, the material of the sleeve is chosen to be stretchable so as to maintain a close fit over the stent during deployment. Suitable materials for implementing the bioresorbable sleeve include, but are not limited to, PLC (70 L/30 C) (L-lactide/ε-caprolactone) or PC Poly(ε-caprolactone) or any other suitable bio-absorbable polymer.

In certain particularly preferred implementations, the outer sleeve 88 may be impregnated with one or more medication which will be slowly released after deployment.

As discussed above, in the open state, according to certain preferred embodiments, the metallic struts cover a sector of significantly less that the entire circumference of the vessel wall. Hence, after the degradation of the sleeve, a significant, contiguous linear segment (or swath) of the vessel remains unexposed to the metal.

Turning now to the remaining drawings, FIGS. 10A-18C illustrate various aspects of the structure and operation of certain preferred embodiments of the present invention. Of particular note is the varying/graduated lengths of the branches (ribs) 30, 40 of the stent as a function of position along the axial length of the stent. Specifically, in the examples illustrated in these figures, the length of the laterally projecting branches 30, 40 is modulated in a wave-like (undulating) manner such that, when deployed, some regions of the stent extend around a majority of the periphery of the vessel (typically between 190° and 330°) while other regions of the stent have significantly shorter branches which extend around only a minority of the periphery of the vessel. This arrangement further reduces the contact area between the metal structure of the stent and the vessel wall.

The aforementioned structure may be viewed as a modification of the series of wide lateral projections similar to those of FIGS. 1-6 and 16A-16B where each wide projection is subdivided into a series of narrow strips which approximate the same overall footprint of support to the vessel wall but which have a greatly reduced actual contact area. The conceptual progression from wide lateral projections to sets of narrow strips is illustrated in FIGS. 16A-17C, where 16A and 16B represent the conceptually equivalent wide-projection structure, and 17A-17C illustrate the conceptual progression towards implementing the alternative narrow-strip structure of FIG. 17C, thereby greatly reducing the overall fraction of contact area per unit area supported by the structure. This structure also facilitates provision of strips 30, 40 on both sides of the backbone 20 to provide generally symmetrical support of the vessel wall. The thin strips can be staggered so that the tips of each strip lie in an interdigitated configuration (preferably without contact between the strips) in the closed state of the structure.

Figures 14, 15:
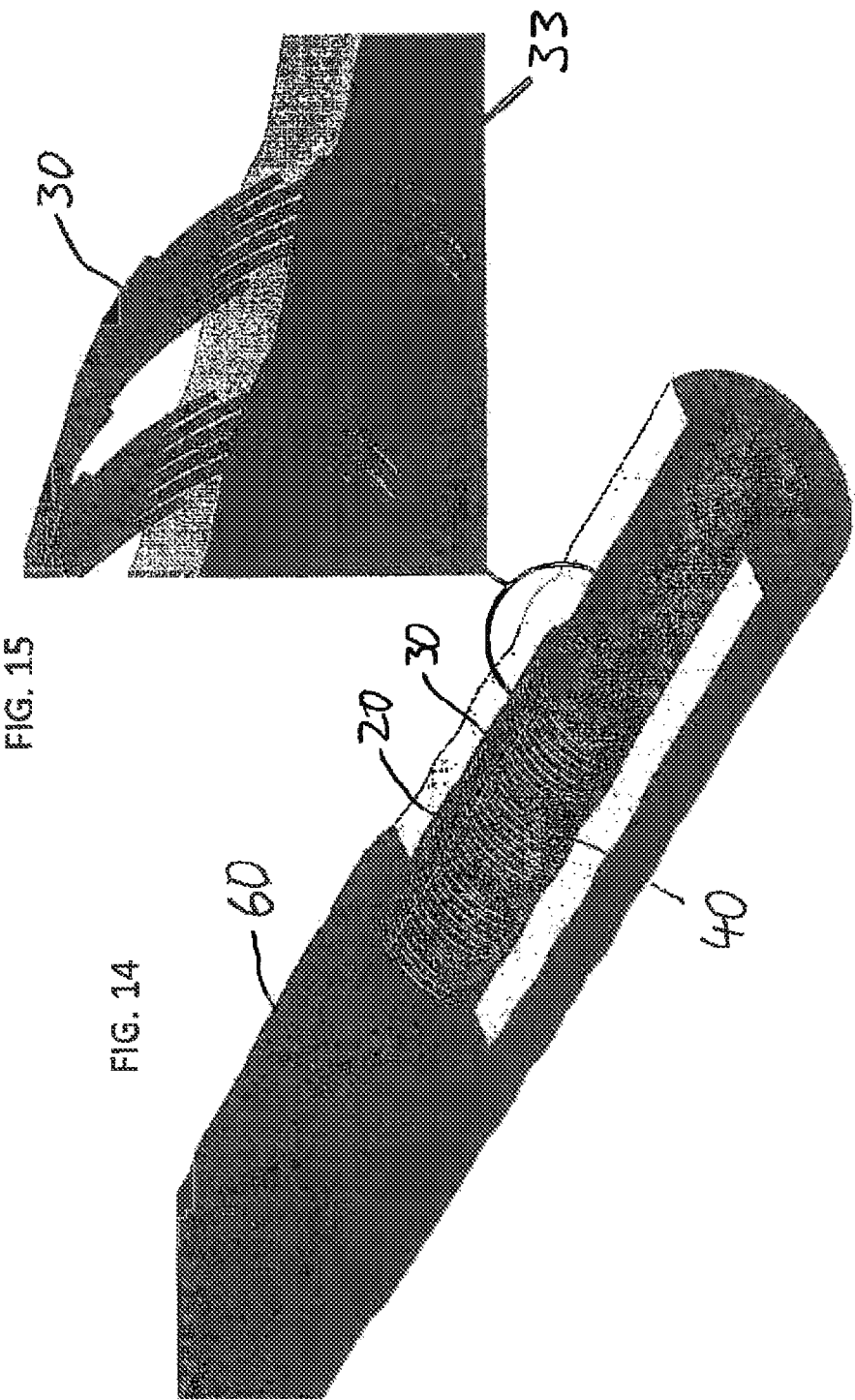
FIGS. 14 and 15 are views similar to FIGS. 13B and 13C illustrating a further optional feature of the present invention.
Figure 16:
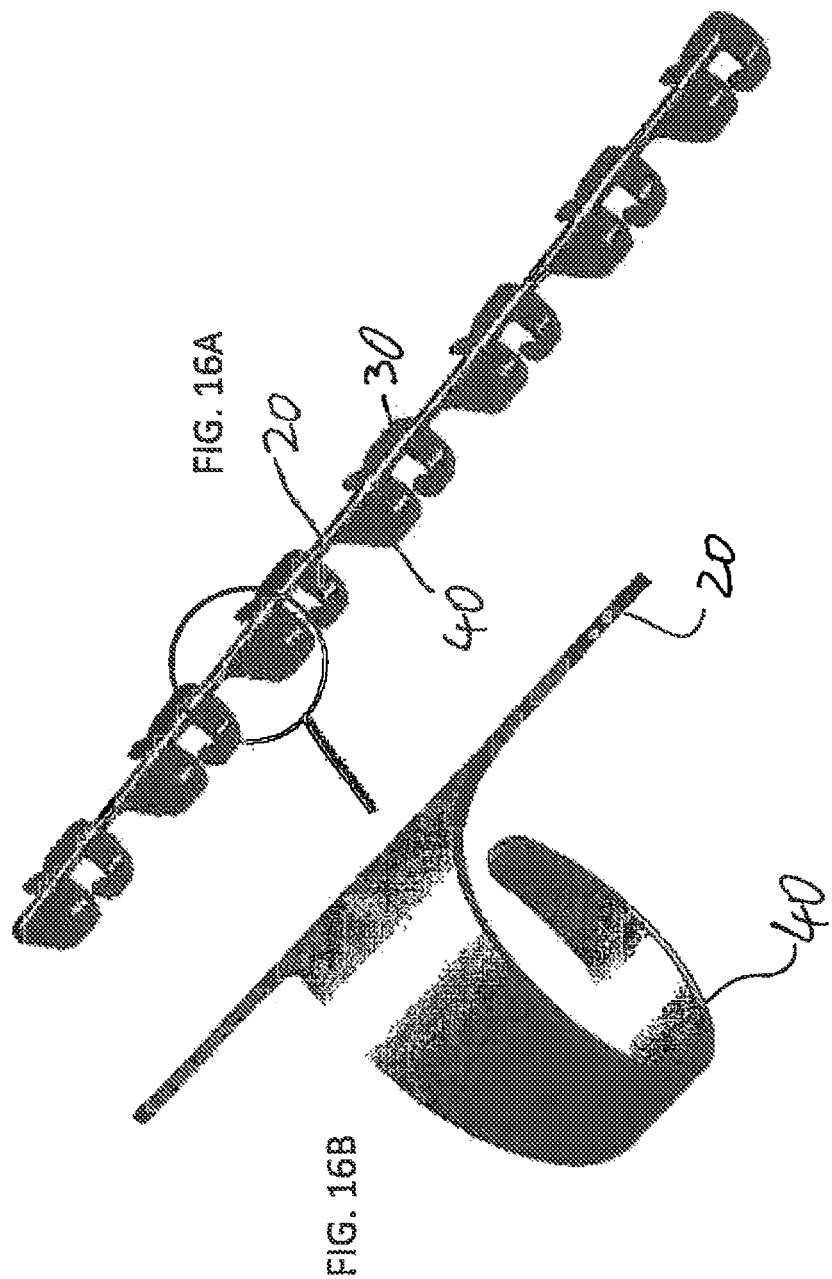
FIGS. 16A, 16B, 17A, 17B and 17C are schematic isometric views illustrating the design principles for achieving a low contact surface stent structure with a given overall contact profile.
Figure 17:
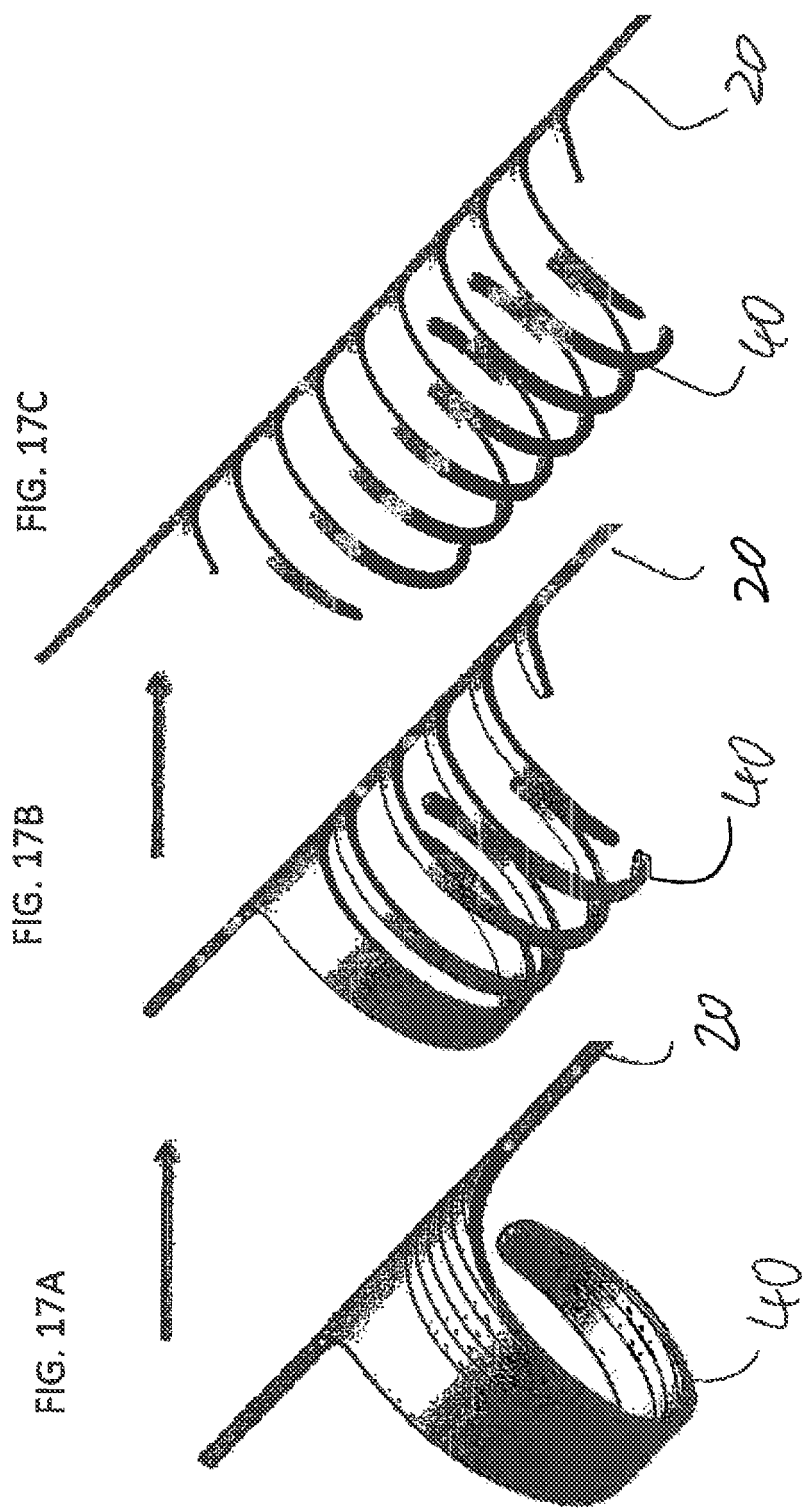
Figure 18:
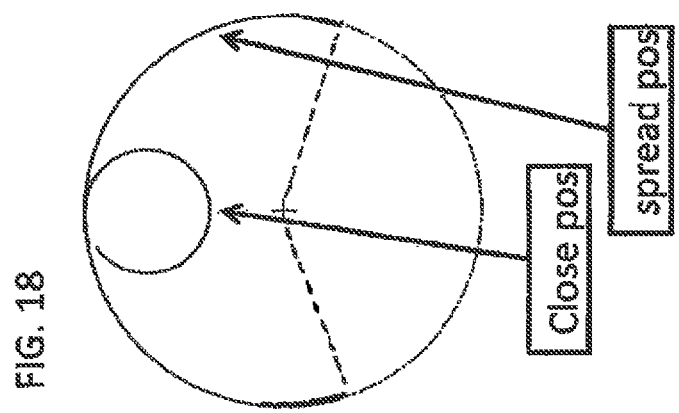
FIG. 18 is a schematic illustration showing the relative diameters of the initial state and the deployed state of an embodiment of the present invention.

A further optional feature illustrated in FIGS. 14 and 15 is the provision of lateral projections which have inwardly curled tips 33 to the rib strips which do not plastically deform (or deform less than the remainder of the ribs) during expansion of the stent, and thereby maintain a smaller radius of curvature than the main part of the stent. This helps to protect the vessel wall from damage by the tips of the narrow strips making up the stent. An example of such curled tips 33 is shown in FIG. 15.

While the invention has been described with respect to a limited number of embodiments, it will be appreciated that many variations, modifications and other applications of the invention may be made. Therefore, the claimed invention as recited in the claims that follow is not limited to the embodiments described herein.

What is claimed is:

1. A stent kit comprising:
   (a) a stent comprising an expandable structure including a plurality of ribs, said expandable structure assuming an initial state in which said ribs lie substantially on a virtual cylinder of a first diameter, said expandable structure being configured for plastic deformation to an open state in which said ribs lie substantially on a virtual cylinder of a second diameter greater than said first diameter; and
   (b) a stent-opening balloon to be inflated within said stent to open said stent from said initial state to said open state, said balloon having a predefined fully inflated state defining said open state of said stent,
   wherein said stent is configured such that, in said open state, said ribs do not span an entirety of said virtual cylinder of said second diameter, leaving a continuous swath along said virtual cylinder free from the stent,
   and wherein tips of said ribs remain inwardly curled relative to said virtual cylinder of a second diameter.

2. The stent kit of claim 1, wherein said stent comprises an elongated backbone defining a direction of elongation,
   and wherein said plurality of ribs are interconnected with said backbone and project therefrom in a direction perpendicular to said direction of elongation,
   wherein said ribs are parallel sided or tapering away from said backbone, and wherein each of said ribs follows a curve lying in a plane perpendicular to said direction of elongation.

3. The stent kit of claim 2, wherein said ribs are mechanically interconnected solely via said backbone.

4. The stent kit of claim 2, wherein each of said ribs is untethered other than its attachment to said backbone.

5. The stent kit of claim 2, wherein said plurality of ribs project from both sides of said backbone in staggered relation, and wherein, in said initial state, ends of at least a subset of said ribs are interdigitated.

6. The stent kit of claim 2, wherein lengths of said ribs vary in an undulating pattern along a length of said backbone.

7. The stent kit of claim 2, further comprising a flexible sleeve deployed around said backbone and said plurality of ribs, said flexible sleeve being formed from biodegradable material.

8. The stent kit of claim 1, wherein said continuous swath spans an angle of between 30 degrees and 170 degrees about a central axis of the stent.

9. The stent kit of claim 1, wherein said continuous swath spans an angle of between 90 degrees and 160 degrees about a central axis of the stent.

10. The stent kit of claim 1, wherein said ribs form at least part of a lattice structure.

\* \* \* \* \*